United States Patent [19]
Blatt et al.

[11] Patent Number: 5,372,808
[45] Date of Patent: Dec. 13, 1994

[54] METHODS AND COMPOSITIONS FOR THE TREATMENT OF DISEASES WITH CONSENSUS INTERFERON WHILE REDUCING SIDE EFFECT

[75] Inventors: Lawrence M. Blatt, Ventura, Calif.; Milton W. Taylor, Bloomington, Ind.

[73] Assignee: Amgen Inc., Thousand Oaks, Calif.

[21] Appl. No.: 868,916

[22] Filed: Apr. 15, 1992

Related U.S. Application Data

[63] Continuation-in-part of Ser. No. 772,922, Oct. 15, 1991, abandoned, which is a continuation-in-part of Ser. No. 599,206, Oct. 17, 1990, abandoned.

[51] Int. Cl.$^5$ .............................. A61K 37/66
[52] U.S. Cl. ........................ 424/85.4; 424/85.5; 424/85.6; 424/85.7; 530/351
[58] Field of Search ............ 530/351; 424/85.7, 85.6, 424/85.5, 85.4

[56] References Cited

U.S. PATENT DOCUMENTS

| | | | |
|---|---|---|---|
| 4,695,623 | 9/1987 | Stabinsky | 530/351 |
| 4,897,471 | 1/1990 | Stabinsky | 530/351 |

OTHER PUBLICATIONS

Curless, C. et al., (1990) Effect of Preinduction Specific . . . BIOtechnology Progress 6:149–152.
Lu, H. S. et al., Structural Modification of Recombinant . . . Analytical Methodologies pp. 449–152.
Moochhala, S. M. et al., Induction and Depression of Cytochrome . . . Biochemical Pharmacology vol. 38, 3:439–447 (1989).
Altrock et al., (1986) Antiviral and Antitumor Effects . . . J. of Interferon Research 6:405–415.
Glaspy, J. A. et al., (1992) Treatment of Hairy Cell Leukemia . . . J. of Immunotherapy 11:198–208 (Apr. 3, 1992).
Ozes, O. N.. et al., (1992) A Comparison of Interferon--Con 1 . . . J. of Interferon Research 12:55–59 (Feb. 1992).
Fish, E. N. et al., (1989) The Role of Three Domains in the Biological Activity . . . , J. of Interferon Research 9:97–114.
Klein, M. L. et al., (1990) Isolation and Structural Characterization of Three Isoforms . . . , Archives of Biochemistry & Biop V.276, 2:531–537.
Fish, E. N. et al., (1986) Antiherpetic Effects of a Human . . . Antimicrobial Agents and Chemotherapy, pp. 52–56.

Primary Examiner—Robert J. Hill, Jr.
Assistant Examiner—Shelly Guest Cermak
Attorney, Agent, or Firm—Robert R. Cook; Craig A. Crandall

[57] ABSTRACT

Methods for the treatment of cell proliferation disorders, viral infections, and other conditions without causing significant side effects normally associated with interferon therapy, involving administering to a patient in need thereof a therapeutically effective amount of consensus human leukocyte interferon are disclosed. Also disclosed are pharmaceutical compositions of consensus human leukocyte interferon.

16 Claims, 8 Drawing Sheets

METHODS AND COMPOSITIONS FOR THE TREATMENT OF DISEASES WITH CONSENSUS INTERFERON WHILE REDUCING SIDE EFFECT

This is a continuation-in-part of copending application Ser. No. 07/772,922 filed on Oct. 15, 1991, now abandoned, which is a CIP of patent application Ser. No. 07/599,206 filed on Oct. 17, 1990, now abandoned.

The present invention relates to methods of treatment of diseases using consensus human leukocyte interferon. The invention also relates to pharmaceutical compositions of consensus human leukocyte interferon that are suitable for the treatment of diseases.

BACKGROUND OF THE INVENTION

Interferons are a subclass of cytokines that exhibit both antiviral and antiproliferative activity. On the basis of biochemical and immunological properties, human interferons are grouped into three classes: interferon-alpha (leukocyte), interferon-beta (fibroblast) and interferon-gamma (immune). At least fourteen alpha interferons (grouped into subtypes A through H) having distinct amino acid sequences have been identified by isolating and sequencing DNA encoding these polypeptides. Alpha interferons have received considerable attention as potential therapeutic agents due to their antiviral and antitumor growth inhibition.

The purification of interferon from human leukocytes isolated from the buffy coat fraction of whole blood is described in U.S. Pat. No. 4,503,035. Human leukocyte interferon prepared in this manner contains a mixture of different human leukocyte interferon amino acid sequences. The purified material has a specific activity of from $0.9 \times 10^8 - 4 \times 10^8$ units/mg. of protein when assayed on the MDBK bovine cell line and from $2 \times 10^6 - 7.6 \times 10^8$ units/mg. of protein when assayed on the Ag 1732 human cell line.

The cytopathic effect inhibition assay used to determine interferon anti-viral activity is disclosed in U.S. Pat. No. 4,241,174. The measured interferon activity was calibrated against a reference standard for human leukocyte interferon provided by the National Institutes of Health.

The construction of recombinant DNA plasmids containing sequences encoding at least part of human leukocyte interferon and the expression in E. coli of a polypeptide having immunological or biological activity of human leukocyte interferon is disclosed in U.S. Pat. No. 4,530,901.

The construction of hybrid alpha-interferon genes containing combinations of different subtype sequences (e.g., A and D, A and B, and A and F) is disclosed in U.S. Pat. Nos. 4,414,150, 4,456,748, and 4,678,751.

U.S. Pat. Nos. 4,695,623 and 4,897,471 disclose novel human leukocyte interferon polypeptides having amino acid sequences which include common or predominant amino acids found at each position among naturally-occurring alpha interferon subtype polypeptides and are referred to as consensus human leukocyte interferon (IFN-con). The IFN-con amino acid sequences disclosed are designated IFN-con$_1$, IFN-con$_2$, and IFN-con$_3$. The preparation of manufactured genes encoding IFN-con and the expression of said genes in E. Coli are also disclosed.

A purification of IFN-con$_1$ produced in E. Coli is described in Klein et al. (*J. Chromatog.* 454, 205-215 (1988)). IFN--con$_1$ purified in this manner is reported to have a specific activity of $3 \times 10^9$ units/mg. protein as measured in the cytopathic effect inhibition assay using the T98G human cell line (Fish et al. *J. Interferon Res.* 4, 97-114 (1989)). Purified IFN-con$_1$ comprises three isoforms as determined by isoelectric focusing which have been identified as methionyl IFN-con$_1$, des-methionyl IFN-con$_1$ and des-methionyl IFN--con$_1$ with its N-terminus blocked by an acetyl group. (Klein et al. *Arch. Biochem. Biophys.* 276, 531-537 (1990)) .

Alpha-interferon is currently approved in the United States and other countries for the treatment of hairy cell leukemia, venereal warts, Kaposi's Sarcoma (a cancer commonly afflicting patients suffering from Acquired Immune Deficiency Syndrome (AIDS)), and chronic non-A, non--B hepatitis. Two variants of alpha interferon have received approval for therapeutic use: Interferon alfa-2a, marketed under the trade name Roferon®-A, and Interferon alfa-2b, marketed under the trade name INTRON® A. The amino acid sequences of Roferon®-A and INTRON® A differ at a single position but otherwise are identical to the amino acid sequence of alpha-interferon subtype 2 (subtype A).

In addition to the labeled indications, alpha-interferon is being used or evaluated alone or in conjunction with chemotherapeutic agents in a variety of other cellular proliferation disorders, including chronic myelogenous leukemia, multiple myeloma, superficial bladder cancer, skin cancers (basal cell carcinoma and malignant melanoma), renal cell carcinoma, ovarian cancer, low grade lymphocytic and cutaneous T cell lymphoma, and glioma. Alpha-interferon may be effective in combination with other chemotherapy agents for the treatment of solid tumors that arise from lung, colorectal and breast cancer (see Rosenberg et al. "Principles and Applications of Biologic Therapy" in *Cancer: Principles and Practices of Oncology*, 3rd ed., Devita et al . , eds . pp. 301-547 (1989) , Balmer *DICP, Ann Pharmacother* 24, 761-768 (1990)) .

Alpha-interferons are known to affect a variety of cellular functions, including DNA replication and RNA and protein synthesis, in both normal and abnormal cells. Thus, cytotoxic effects of interferon are not restricted to tumor or virus infected cells but are also manifested in normal, healthy cells as well. As a result, undesirable side effects arise during interferon therapy, particularly when high doses are required. Administration of interferon can lead to myelosuppression resulting in reduced red blood cell, white blood cell and platelet levels. Higher doses of interferon commonly give rise to flu-like symptoms (e.g., fever, fatigue, headaches and chills), gastrointestinal disorders (e.g., anorexia, nausea and diarrhea), dizziness and coughing. It would be useful to reduce or eliminate the undesirable side effects of interferon therapy without diminishing the therapeutic benefits of such therapy.

Therefore, an object of this invention is the treatment of conditions that are susceptible of treatment with an interferon, wherein the undesirable side effects normally associated with alpha interferon treatment are significantly diminished compared to currently practiced treatment regimens or eliminated entirely. Another object of the invention is to achieve enhanced therapeutic benefit in the treatment of diseases with interferon as compared to currently practiced regimens, with substantially no corresponding increase in the frequency or severity of undesirable side effects.

SUMMARY OF THE INVENTION

The invention encompasses methods of treatment of various conditions susceptible of treatment with an interferon, involving administering to a mammal, preferable a human, a therapeutically effective amount of consensus human leukocyte interferon (IFN-con). The invention is based on the discovery that IFN-con does not cause the same degree of side effects in patients as do alpha interferons. The conditions that may be treated in accordance with the present invention are generally those that are susceptible to treatment by alpha interferons. In other words, IFN-con is useful to treat substantially the same conditions that may be treated with alpha interferons, such as Intron® A. Exemplary conditions include, but are not limited to, cell proliferation disorders and viral infections. IFN-con is effective in treating cell proliferation disorders frequently associated with cancer. Such disorders include, but are not limited to, hairy cell leukemia and Kaposi's Sarcoma. IFN-con may be used alone or in combination with other therapeutics for the treatment of cancer and other proliferative disorders. In a preferred embodiment, IFN-con is used in conjunction with a therapeutically effective amount of one or more factors that stimulate myeloid cell proliferation or differentiation, such as granulocyte colony stimulating factor (G-CSF), granulocyte/ macrophage colony stimulating factor (GM-CSF), interleukin-1 (IL-1), interleukin-3 (IL-3), interleukin-6 (IL-6), erythropoietin, and stem cell factor (SCF). G-CSF is a preferred factor for use with IFN-con.

Viral conditions treatable by IFN-con include, but are not limited to, hepatitis A, hepatitis C, other non-A, non--B hepatitis, hepatitis B, herpes virus (EB, CML, herpes simplex), papilloma, poxvirus, picorna virus, adeno virus, rhino virus, HTLV I, HTLV II, and human rotavirus.

Although it has previously been appreciated that the above conditions can be treated with alpha interferon, side effects accompanying such treatment have severely limited the overall usefulness of such treatment. In some cases, such as Epstein-Barr infection, side effects accompanying alpha interferon treatment have virtually ruled out treatment using alpha interferon. Thus, for purposes of the present invention, conditions that can be treated with IFN-con include those conditions in which alpha interferon treatment shows some efficacy, but which may not be treatable with known interferons because the negative side effects outweigh the benefits of the treatment. It has now been discovered and disclosed herein that treatment with a non-naturally occurring interferon, selected from consensus human leukocyte interferons (IFN-con) results in substantially reduced or eliminated side effects as compared to treatment with alpha interferon. The reduction or elimination of side effects is expected to be demonstrated regardless of the condition being treated. The reduction or elimination of side effects discovered for IFN-con could not have been predicted based on the results reported in the prior art. The actual clinical results presented herein clearly demonstrate not only that IFN-con causes reduced or non-existent side effects at the same dose level as alpha interferon, but that 3 to 5 times more IFN-con may be administered without causing dose-limiting side effects.

Additionally, it is shown below that IFN-con has similar or higher activity than INTRON® A in the above described indications. In particular, IFN-con shows higher antiproliferative activity than IN-TRON® A. Therefore, treatment of a cell proliferation disorder using IFN-con shows enhanced efficacy and safety compared to other currently practiced interferon treatments. The administration of a therapeutically effective amount of IFN-con results in more rapid or more extensive treatment of a cellular proliferative disorder compared to currently practiced methods, wherein no corresponding increase in the frequency or severity of associated undesirable side effects occurs. In addition, a therapeutically effective amount of IFN-con may be less than the amount of an interferon used in currently practiced regimens. As a result, in some cases, a decreased dose of IFN-con gives the same therapeutic benefit as higher doses of other interferons but with a decrease or elimination of undesirable side effects associated with currently practiced interferon therapy.

IFN-con is a nonnaturally-occurring polypeptide having antiproliferative activity. Preferably, IFN-con is a polypeptide having the amino acid sequence of IFN-con$_1$, IFN-con$_2$, or IFN-con$_3$. Most preferably, IFN-con has the amino acid sequence of IFN-con$_1$.

The invention also relates to pharmaceutical compositions comprising a therapeutically effective amount of IFN-con along with suitable diluents, adjuvants, carriers, preservatives and/or solubilizers.

DETAILED DESCRIPTION OF THE INVENTION

Figure 1:
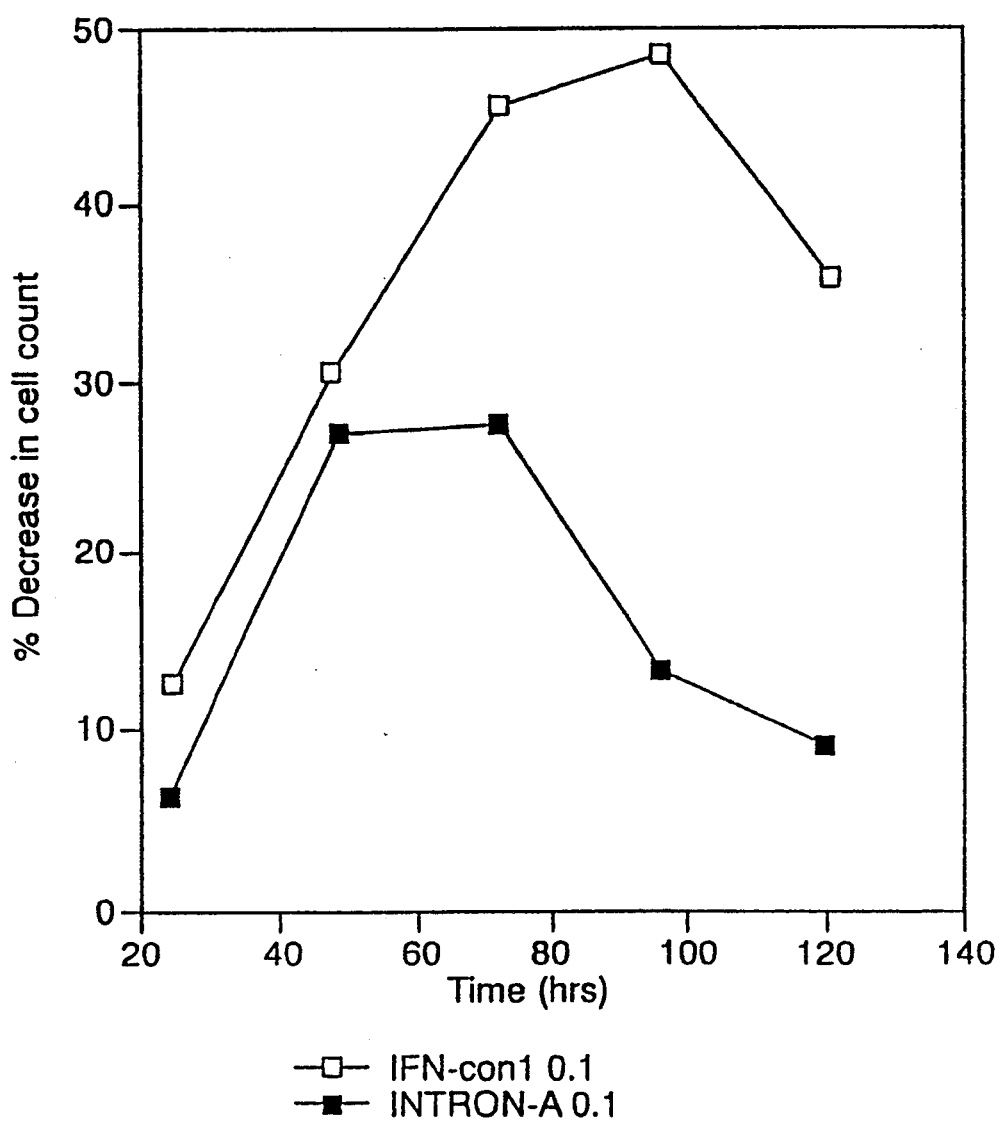
FIG. 1 shows the antiproliferative activity of IFN-con$_1$ and INTRON®A, a comparative material, on Eskol, a hairy cell leukemic cell line, when interferons were added to an Eskol cell suspension at 0.1 ngs/ml.
Figure 2:
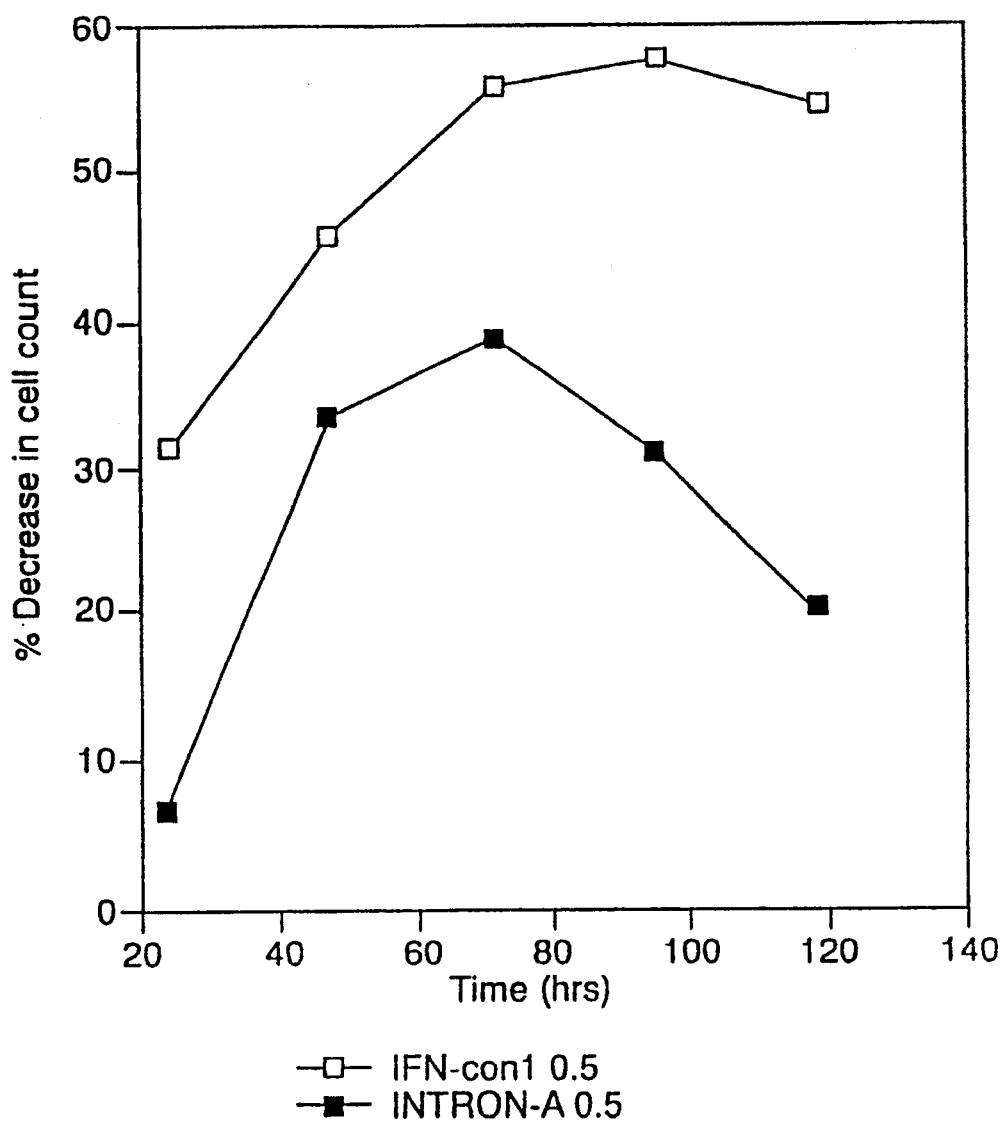
FIG. 2 shows the antiproliferative activity of IFN-con$_1$ and INTRON®A, a comparative material, on Eskol, a hairy cell leukemic cell line, when interferons were added to an Eskol cell suspension at 0.5 ngs/ml.
Figure 3:
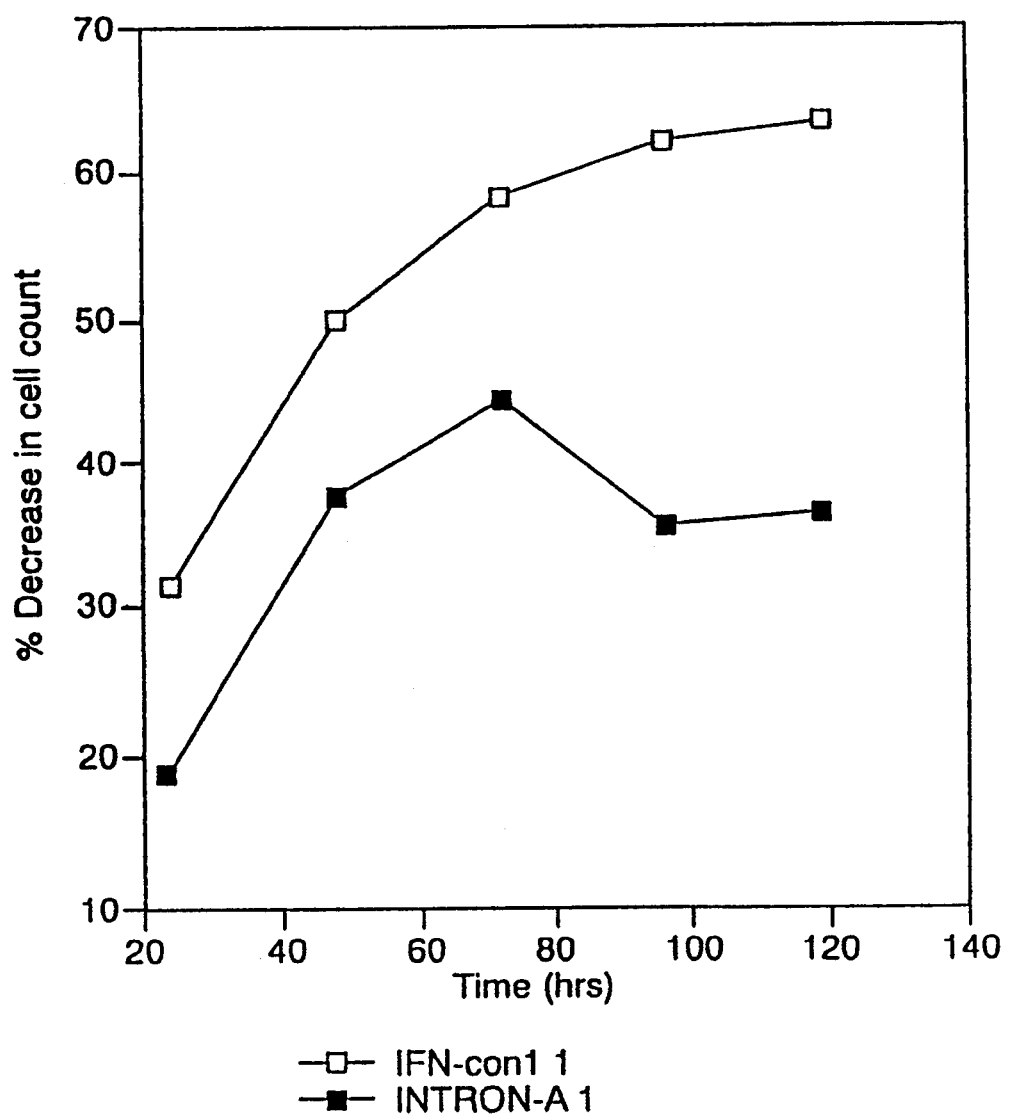
FIG. 3 shows the antiproliferative activity of IFN-con$_1$ and INTRON® A, a comparative material, on Eskol, a hairy cell leukemic cell line, when interferons were added to an Eskol cell suspension at 1.0 ngs/ml.
Figure 4:
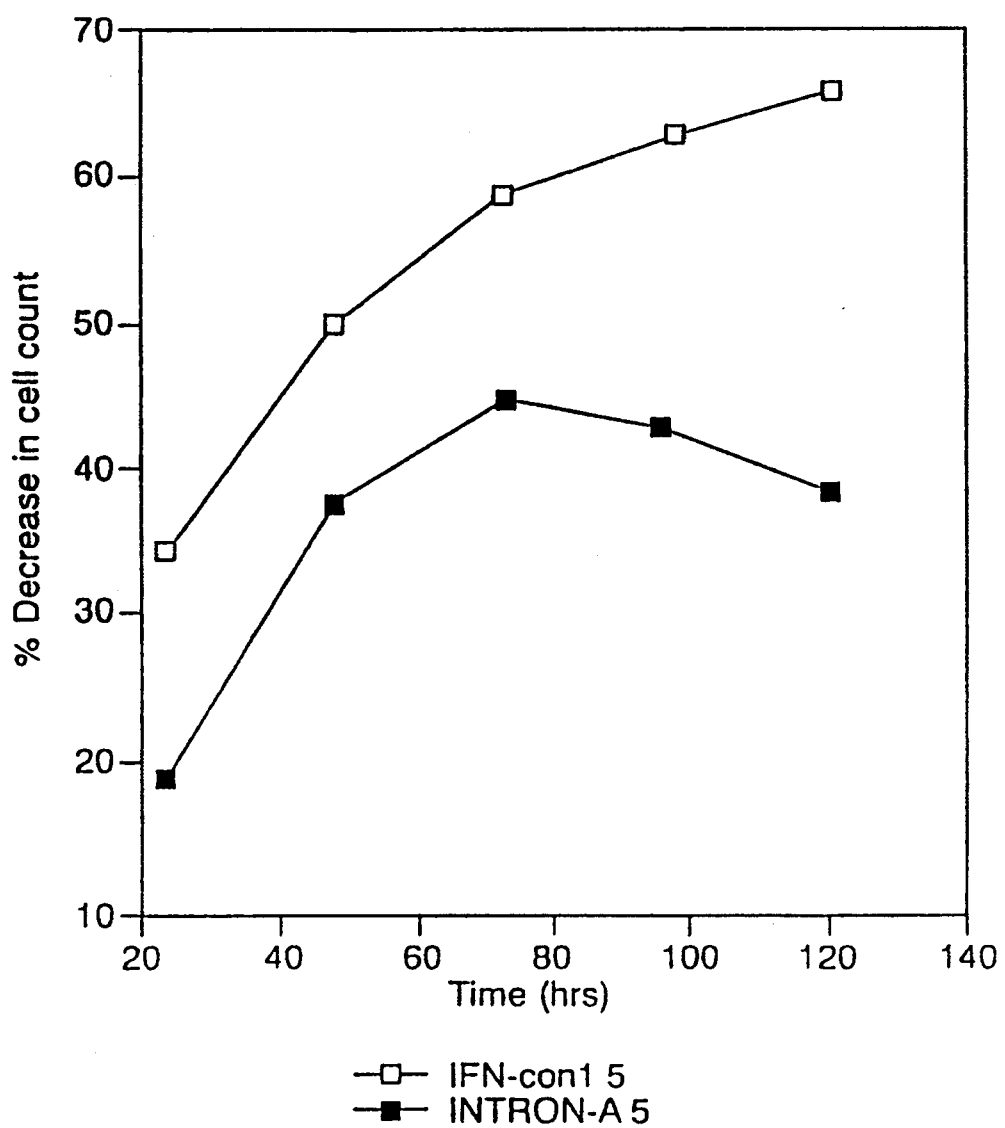
FIG. 4 shows the antiproliferative activity of IFN-con$_1$ and INTRON® A, a comparative material, on Eskol, a hairy cell leukemic cell line, when interferons were added to an Eskol cell suspension at 5.0 ngs/ml.
Figure 5:
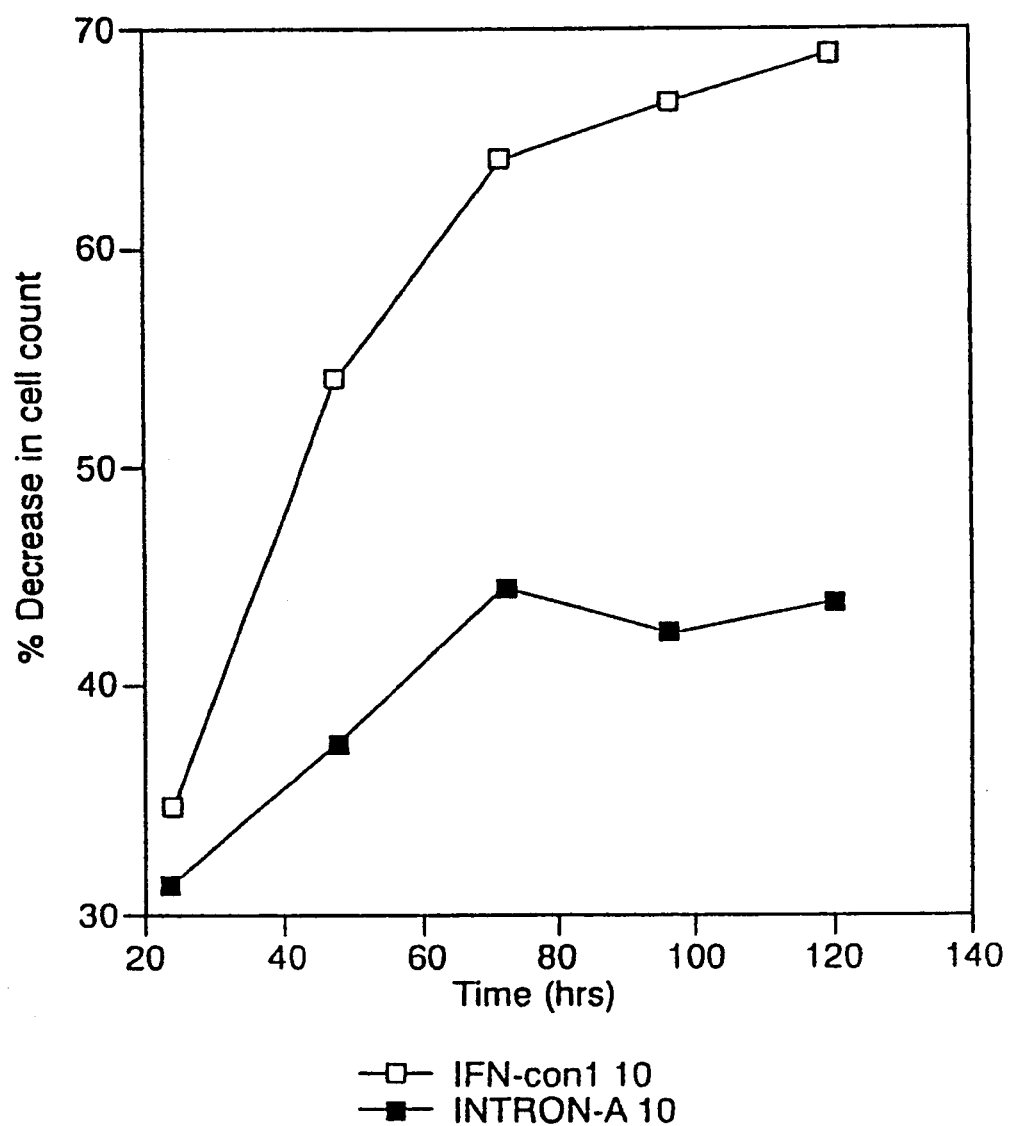
FIG. 5 shows the antiproliferative activity of IFN-con$_1$ and INTRON® A, a comparative material, on Eskol, a hairy cell leukemic cell when interferons were added to an Eskol cell suspension at 10 ngs/mi.
Figure 6:
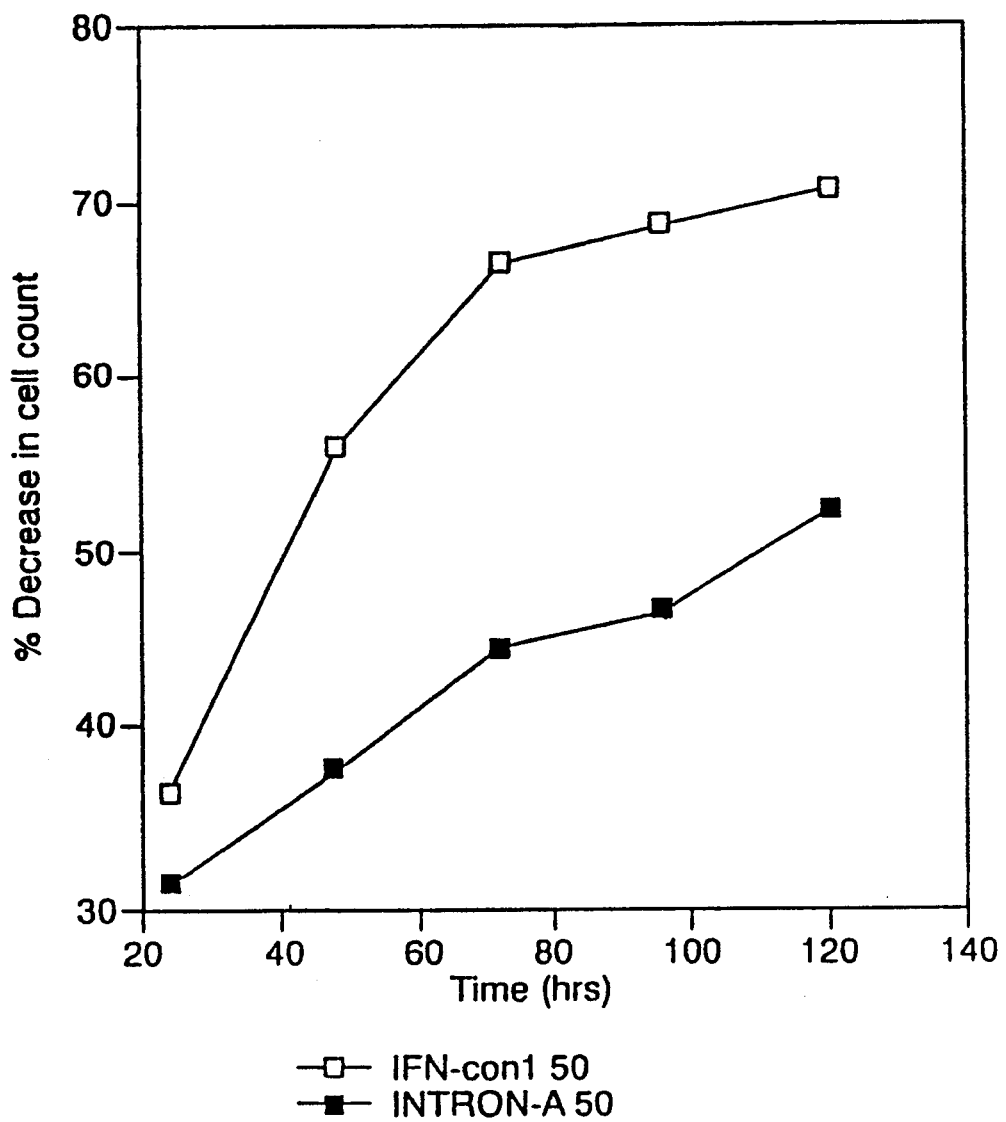
FIG. 6 shows the antiproliferative activity of IFN-con$_1$ and INTRON®A, a comparative material, on Eskol, a hairy cell leukemic cell line, when interretorts were added to an Eskol cell suspension at 50 ngs/ml.
Figure 7:
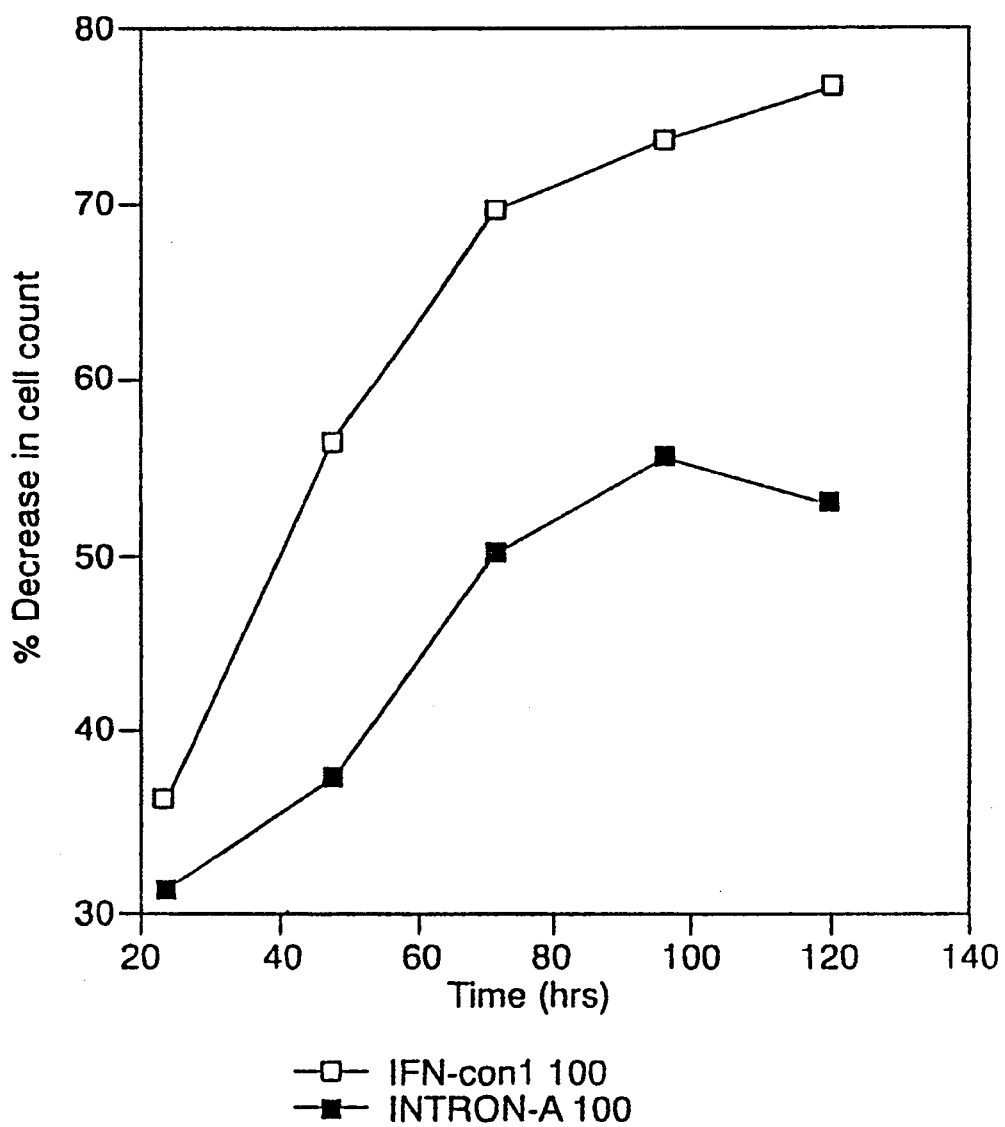
FIG. 7 shows the antiproliferative activity of IFN-con$_1$ and INTRON® A, a comparative material, on Eskol, a hairy cell leukemic cell line, when interferons were added to an Eskol cell suspension at 100 ngs/ml.

As employed herein, consensus human leukocyte interferon (IFN-con) means a nonnaturally-occurring polypeptide, which predominantly includes those amino acid residues that are common to all naturally-occurring human leukocyte interferon subtype sequences and which includes, at one or more of those positions where there is no amino acid common to all subtypes, an amino acid which predominantly occurs at that position and in no event includes any amino acid residue which is not extant in that position in at least one naturally-occurring subtype. IFN-con encompasses but is not limited to the amino acid sequences designated IFN-con$_1$, IFN-con2 and IFN--con$_3$ which are disclosed in commonly owned U.S. Pat. Nos. 4,695,623 and 4,897,471, the entire disclosures of which are hereby incorporated by reference. DNA sequences encoding IFN-con may be synthesized as described in the above-mentioned patents or other standard methods.

IFN-con polypeptides are preferably the products of expression of manufactured DNA sequences transformed or transfected into bacterial hosts, especially E. coli. That is, IFN-con is recombinant IFN-con. IFN-con is preferably produced in E. coli is purified by procedures known to those skilled in the art and generally described in Klein et al., supra (1988) for IFN-con$_1$. Purified IFN--con may comprise a mixture of isoforms, e.g., purified IFN-con$_1$ comprises a mixture of methlonyl IFN-con$_1$, des-methionyl IFN-con$_1$ and des-methionyl IFN--con$_1$ with a blocked N-terminus (Klein et al., supra (1990)). Alternatively, IFN-con may comprise a specific, isolated isoform. Isoforms of IFN-con are separated from each other by techniques such as isoelectric focusing which are known to those skilled in the art.

The subject invention provides for a method of treating a condition treatable by alpha interferon while reducing or eliminating one or more side effects typically associated with alpha interferon treatment, involving administering a therapeutically effective amount of IFN-con to a patient. A preferred embodiment of the invention is a method of treatment involving administering a therapeutically effective amount of IFN-con$_1$, IFN-Con$_2$, or IFN--con$_3$. Most preferably, a therapeutically effective amount of IFN-con$_1$ is administered.

The phrase "reducing or eliminating one or more side effects associated with interferon administration,, is believed to be clear and understandable to those of ordinary skill in the relevant art. Generally, one may use any of a variety of measures of number and degree of severity of side effects associated with interferon therapy to determine whether the side effect profile is different from one interferon to another. One suitable interferon for comparative purposes with consensus interferon is Intron® A, interferon alfa-2b, sold by Schering-Plough.

A convenient way of rating severity of side effects is to use a standard scale such as that accepted by the WHO (World Health Organization). The scale, which is currently widely used by clinicians, utilizes grade levels of side effects as follows: grade I, mild; grade II, moderate; grade III, severe; grade IV, life threatening. Although there is some subjectivity involved in these ratings, if the same clinician is rating groups of patients, a comparison of side effect profiles between two drugs may be valid and acceptable to doctors. To make a comparison, doctors will frequently look at whether administering a given drug at a given dose level results in a dose-limiting toxicity (DLT). A DLT occurs when a patient judges a side effect as intolerable. When this occurs, a doctor may either reduce the dose (typically by 3 million units in the case of Intron® A or consensus interferon) or take the patient off of the drug for a period of time followed by resuming administration at the same or a lower dose. In any case, when a DLT is encountered, the result can be a sub-optimal treatment regime with less than optimal efficacy. Thus, another way of expressing a reduction in side effects is to refer to a reduced number of DLT's at a given dose level. A comparison of DLT's is presented for Intron® A and consensus interferon in Example 3. Although other measures of side effect profiles may be employed, the result is the same: as compared to other interferons, especially alpha interferons such as Intron® A and Roferon® (Hoffmann La Roche), consensus interferon results in fewer DLT's and, generally, a patient that feels better at all dose levels that are useful to treat diseases.

Suitable conditions for treatment with IFN-con include a variety of cell proliferation disorders, particularly various cancers. These disorders include, but are not limited to, hairy cell leukemia, Kaposi's Sarcoma, chronic myelogenous leukemia, multiple myeloma, superficial bladder cancer, skin cancer (basal cell carcinoma and malignant melanoma), renal cell carcinoma, ovarian cancer, low grade lymphocytic and cutaneous T cell lymphoma, and glioma.

Other conditions suitable for treatment with IFN-con include a variety of viral diseases. These diseases include, but are not limited to, hepatitis A, hepatitis B, hepatitis C, non-A, non--B hepatitis (other than hepatitis B or C), Epstein-Barr viral infection, HIV infection, herpes virus (EB, CML, herpes simplex), papilloma, poxvirus, picorna virus, adeno virus, rhino virus, HTLV I, HTLV II, and human rotavirus.

IFN-con may be used alone or in combination with other therapeutics for the treatment of the indications described herein. For example, IFN-con may be administered in conjunction with a therapeutically effective amount of one or more chemotherapy agents such as busulfan, 5-fluoro-uracil (5--FU), zidovudine (AZT), leucovorin, melphalan, prednisone, cyclophosphamide, dacarbazine, cisplatin, and dipyridamole. IFN-con may also be given in conjunction with cytokines such as interleukin-2 (IL-2).

A therapeutically effective amount of IFN-con may be administered in combination with a therapeutically effective amount of one or more factors that stimulate myeloid differentiation so as to overcome the effects of myelosuppression observed during interferon treatments. Such agents include, but are not limited to, G-CSF, GM-CSF, IL-1, IL-3, IL-6, erythropoietin and SCF. Stem cell factor (SCF) stimulates the proliferation of early hematopoietic progenitor cells and has been described in patent application Ser. No. 573,616, the disclosure of which is hereby incorporated by reference. A preferred agent is G-CSF.

In Examples 1–3 provided below, it is shown that IFN-con$_1$ is an effective antiproliferative agent against hairy cell leukemia and AIDS-associated Kaposi's Sarcoma.

The anti-proliferative activity of IFN--con$_1$ and INTRON® A assayed on Eskol cells, a hairy cell leukemic cell line, is shown in Example 1. It is shown that IFN-con$_1$ has greater anti-proliferative activity than Intron® A over a wide range of concentrations. Similar results were obtained when IFN-con$_1$ was compared to Roferon®-A. These results indicate that IFN-con$_1$ has greater therapeutic efficacy when administered at the same concentrations as Intron® A. Alternatively, lower concentrations of IFN-con$_1$ are required to demonstrate therapeutic efficacy equivalent to that of Intron ® A.

Example 2 describes a comparative study of IFN-con1 and INTRON-A in the treatment of AIDS-associated Kaposi's Sarcoma. It was shown that patients receiving IFN-con1 achieved higher unit doses than those patients receiving INTRON-A. In addition, patients receiving both and IFN-con1 and GCSF achieved higher doses of IFN-con1 than those patients receiving IFN-con1 alone (see FIG. 8). In this study, all patients received AZT as part of their treatment of HIV infection. AZT administered alone is not effective on Kaposi's Sarcoma.

IFN-con1 was demonstrated to be safer than INTRON-A as judged by the reduced frequency of Grade 3 toxicity when IFN-con1 was administered. Treatment with IFN-con1 showed a reduced incidence of neutropenia and liver dysfunction compared to INTRON-A treatment while treatment with IFN-con1 and r-metGCSF completely eliminated Grade 3 toxicity (see Table 2).

Example 3 shows data obtained from clinical trials involving patients infected with hepatitis Also provided for are pharmaceutical compositions comprising a therapeutically effective amount of IFN-con together with pharmaceutically acceptable carriers, adjuvants, diluents, preservatives and/or solubilizers. Pharmaceutical compositions of IFN-con include diluents of various buffers (e.g., Tris-HCl, acetate, phosphate) having a range of pH and ionic strength, carriers (e.g., human serum albumin), solubilizers (e.g., tween, polysorbate), and Preservatives (e.g., thimerosol, benzyl alcohol). In general, components of pharmaceutical compositions can be selected from among those commonly employed with interferons and other antiproliferative or antiviral agents and which are known to those skilled in the art. A pharmaceutical composition of IFN-con is supplied as an injectable solution or as a lyophilized powder which is reconstituted in an appropriate diluent prior to injection.

A therapeutically effective amount of IFN-con can be determined by one skilled in the art taking into account such variables as the half-life of IFN-con preparations, route of administration and the condition being tested. In general, a therapeutically effective amount of IFN-con for the treatment of a cell proliferation disorder will be in the range of $2 \times 10^6$ to $60 \times 10^6$ units per patient administered several times per week. Doses in the lower part of the range are effective in the treatment of hairy cell leukemia while doses in the higher part of the range are suitable for the treatment of Kaposi's Sarcoma. Therapeutically effective amounts of IFN-con will preferably result in tumor remission of 20–80% depending upon the specific tumor type for a period of at least six months. In general, a therapeutically effective amount of IFN-con for the treatment of a viral condition will be in the range of $3 \times 10^6$ to $30 \times 10^6$ units, preferably $6 \times 10^6$ to $15 \times 10^6$ units, per patient, administered several times (e.g. , 2–7, preferably 3) per week.

The route of administration will preferably be by injection into the blood of a mammal where the injection may be intravenous, intramuscular, subcutaneous or intralesional. Administration may also be by oral or nasal routes. The suitability of a given pharmaceutical composition for a given route of administration will be apparent to one skilled in the art.

The following examples are offered to more fully illustrate the invention but are not to be construed as limiting the scope thereof.

EXAMPLE 1

Anti-proliferative Activity of IFN-con1 and Intron ® A

The anti-proliferative activity of IFN-con1 and Intron ® A was tested on the Eskol cell line, a hairy cell leukemic cell line isolated by Dr. E. Srour at the Indiana University Medical School. Three ml cultures of Eskol cells were incubated in RPMI medium (Gibco) at 37° C. in 5% $CO_2$ containing 10% fetal calf serum for 12 hours at $1 \times 10^5$ cells/mi. IFN-con1 or Intron ® A (Interferon alfa 2b; Schering Corp.) was added to a final protein concentration of 0.1 to 100 ngs/ml in 100 μl of media. The protein concentration of IFN-con1 was determined by a Bradford protein assay (Bradford, Anal. Biochem. 72, 248–254 (1976)) while the concentration of Intron ® A was calculated from the specific activity ($2 \times 10^8$ International units/mg protein) and unit concentration supplied by the manufacturer. The number of viable cells was determined at 24 hour intervals by exclusion of trypan blue (Sigma). 100 μl of IFN-con1 or Intron ® A were added to the indicated final concentration at 24 hour intervals. Viable cell counts were an average of four independent experiments with each experiment having duplicate samples. Variation in cell counts ranged from about 5% at 24 to 48 hours to about 2% at longer time points. The results shown in FIGS. 1–7 are ratios of viable cell counts in the presence or absence of interferon at various times expressed as percentages.

The viable cell count was confirmed by measuring the incorporation of $^3$H-thymidine into Eskol cells incubated in the presence of IFN-con1 or INTRON-A. After the 120 hour incubation period, a 200 μl cell suspension was withdrawn and incubated at 37° C. for three hours in the presence of 5 μCi/ml $^3$H-thymidine (Amersham). The cells were harvested using a Cambridge cell harvester (Cambridge Technology), washed seven times with distilled water and twice with 95% ethanol and the amount of $^3$H-thymidine incorporated was determined by liquid scintillation counting. The observed uptake of $^3$H-thymidine by Eskol cells incubated for 120 hours in the presence of IFN-con1 or Intron ® A was proportional to the cell viability count.

EXAMPLE 2

Safety, Tolerance and Efficacy of
IFN-con1 Administered to Patients having Kaposi's Sarcoma (KS)

A randomized, open-label study to evaluate the safety and tolerance and to define the maximum tolerated dose (MTD) of IFN-con1 and Intron ® A was undertaken. IFN-con1 and Intron ® A were each administered in combination with zidovudine (AZT) to patients with AIDS-associated KS. In addition, the safety, tolerance and MTD of IFN-con1 was determined when administered in conjunction with AZT and E. coli produced recombinant granulocyte colony stimulating factor having a methionine residue at the amino terminal end of the polypeptide (r-metGCSF). The three treatment groups in the study were:
1. Intron ® A and AZT
2. IFN-con1 and AZT
3 . IFN-con1 , AZT and r-metGCSF.

At least 12 evaluable patients are included in each treatment group.

PRODUCT DESCRIPTION

IFN-con$_1$ was produced in E. coli using methods described in U.S. Pat. Nos. 4,695,623 and 4,897,471. IFN-con$_1$ was purified by procedures generally described in Klein et al., supra (1988). For subcutaneous administration in the current study, IFN-con$_1$ was supplied as a sterile protein solution in sodium phosphate buffer. If required, dilution was made into sterile saline.

Zidovudine (AZT) was purchased from Burroughs-Wellcome Co. and used as directed on the package insert.

Intron® A was purchased from Schering Corp. as a sterile, lyophilized formulation which was resuspended in diluent as directed on the package insert.

r-metGCSF was produced in E. coli using methods generally described in U.S. Pat. No. 4,810,643, the disclosure of which is herein incorporated by reference. r-metGCSF was prepared as a sterile protein solution in 10 mM sodium acetate, 5% mannitol and 0.004% Tween 80 at pH 4.0 at a concentration of 0.3 mg/ml. If required, dilution was made into sterile 5% glucose in water (D$_5$W).

Dosage and Schedules

AZT. AZT was administered to all patients at a fixed dose of 100 mg. orally every four hours while the patient is awake for a total of five doses, or 500 mg, daily.

r-metGCSF. For those patients randomized to the treatment group including r-metGCSF, doses of r-metGCSF were 1 µg/kg body weight per day, administered subcutaneously as a single bolus injection. If necessary, this dosage was increased in increments of 1 µg/kg/day (not to exceed 6 µg/kg/day) or decreased in decrements of 0.5 µg/kg/day or less, as appropriate, in order to achieve the absolute neutrophil count (ANC) target range of 5,000 to 15,000/mm$^3$.

Interferon. Patients received either IFN-con$_1$ or Intron® A according to a dose escalation scheme. Dosage was based upon equal units of either interferon. However, because the specific activities of the two interferons are different ($2 \times 10^8$ IU/mg for Intron® A and at least $1 \times 10^9$ IU/mg for IFN-con$_1$ as determined by the antiviral cytopathic assay described in U.S. Pat. No. 4,695,623), the amount of protein by weight (in mg) at any given dose will be different for Intron® A and IFN-con$_1$. The dose escalation scheme used is shown below in Table 1. The dose in mg of protein corresponding to each dose level in IUs is also shown in Table 1 for each interferon.

TABLE 1

Dose Escalation Schedule for Intron® A and IFN-Con$_1$

| Dose Level | Dose x 10$^6$ IU | Dose in mg Protein INTRON® A | IFN-Con$_1$ |
|---|---|---|---|
| 1 | 3 | 0.015 | 0.003 |
| 2 | 9 | 0.045 | 0.009 |
| 3 | 12 | 0.060 | 0.012 |
| 4 | 15 | 0.075 | 0.015 |
| 5 | 18 | 0.090 | 0.018 |
| 6 | 21 | 0.105 | 0.021 |
| 7 | 24 | 0.120 | 0.024 |
| 8 | 27 | 0.135 | 0.027 |
| 9 | 30 | 0.150 | 0.030 |

Patients in each of the three treatment groups shown above were administered IFN-con$_1$ or INTRON-A starting at dose level 1 daily for one week before escalating to the next highest dose level. Dose escalation occurred on days 8, 15, 22, 29, 36, 43, 50 and 57. Escalation continued until each patient reached an MTD or the maximum daily dose of $30 \times 10^6$ IUs of interferon was achieved. The MTD for an individual patient was defined as the dose level below that at which dose-limiting toxicity occurs. Toxicity was graded on a scale of 0 (no toxicity) to 4 (acute toxicity) using criteria established by the World Health Organization and described further in Miller et al. (Cancer 47, 210–211 (1981). Dose-limiting toxicity was defined as a Grade 3 or Grade 4 adverse event judged to be at least possibly related to interferon. Fever and chills lasting less than 24 hours, fatigue, headache, or Grade 2 or less toxicity were not used in defining the MTD unless they were determined to be intolerable to the individual patient.

At the completion of the escalation phase, patients were continued on maintenance therapy consisting of daily dosing at either the patient's MTD or at the maximum dose of $30 \times 10^6$ IUs if that was achieved. Maintenance therapy was continued until disease progression or other criteria warranted removing the patient from the study.

During maintenance therapy, two interferon dose reductions as a result of toxicity were permitted. After two dose reductions, no further interferon dosing modifications were allowed and patients requiring further reductions were withdrawn from the program. An exception to this procedure was when the dose-limiting toxicity was neutropenia (ANC$\leq$1000/mm$^3$ on two days of an approximately one week period). In this instance, the patient was allowed to remain in the study without further reduction in interferon dose, but r-metGCSF therapy was initiated at 1 µg/kg body weight per day, administered subcutaneously, to patients not receiving r-metGCSF. For patients already in the r-metGCSF treatment group, the dose of r-metGSCF administered was escalated to the next highest level (an increase of 1 µg/kg/day).

Patient Selection

A total of 49 patients have been enrolled in the study. An individual is enrolled in the study only after meeting all inclusion and exclusion criteria. The significant criteria for inclusion are serologically documented HIV infection, histopathologically confirmed Kaposi's Sarcoma with measurable cutaneous or oral lesion(s), acceptable immune function (as measured by CD4 lymphocyte levels) and under AZT treatment for less than one year.

Among the reasons for the withdrawal of a patient from the study are a second occurrence of Grade 3 or greater toxicity during the dose escalation phase, a third occurrence of dose-limiting toxicity after the individual patient's MTD has been determined and the patient is on maintenance therapy, or a progression in KS.

Determination of MTDs for IFN-con$_1$ and Intron® A

Figure 8:
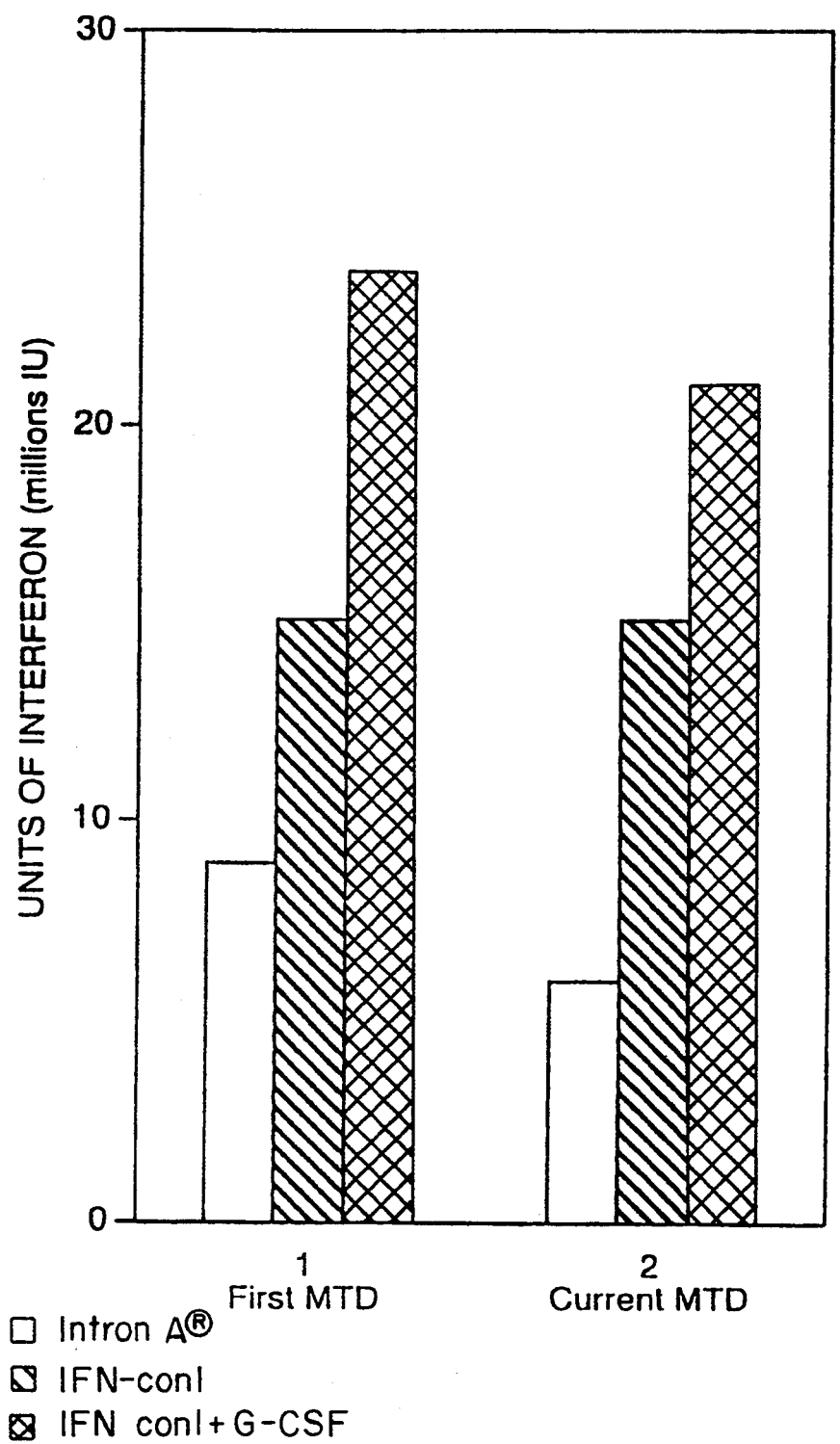
FIG. 8 shows the first and current median MTDs achieved by Kaposi's Sarcoma patients treated with INTRON-A, IFN--Con$_1$, or IFN-Con$_1$ and r-metGCSF.

Using the dose escalation scheme described above for weeks 1–9 of study, followed by maintenance therapy and dose reduction when appropriate, the first and current median MTDs of INTRON-A AND IFN-Con$_1$ for the three treatment groups were determined and are shown in FIG. 8. Each group consists of 15 patients. Group I (Intron® A and AZT) attained a first MTD during dose escalation of $9 \times 10^6$ IUs and a current MTD of $6 \times 10^6$ IUs; Group 2 (IFN-con$_1$ and AZT)

attained first and a current MTDs of $15 \times 10^6$ IUs; and Group 3 (IFN-con$_1$, r-metGCSF and AZT) attained first and current MTDs of $24 \times 10^6$ IUs and $21 \times 10^6$ IUs, respectively.

Evaluation of safety of Intron ® A and IFN-Con$_1$ treatment

The safety of Intron ® A and IFN-Con$_1$ treatment was determined by the severity of adverse effects that required interferon dose reduction. The results are summarized in Table 2.

TABLE 2

Toxicities Prompting Dose Reductions In Three Treatment Groups

| | Frequency of Occurrence (%) | | |
|---|---|---|---|
| | Intron ® A | IFN-Con$_1$* | IFN-Con$_1$ and r-metGCSF* |
| Grade 2 Intolerance (Flu-like syndrome) | 20 | 70 | 65 |
| Grade 3 Neutropenia | 40 | 10 | 0 |
| Grade 3 Liver function tests | 30 | 10 | 0 |

*Percentages for IFN-Con$_1$ and IFN-Con$_1$ and r-metGCSF treatment groups do not add up to 100% because some patients in these groups reached the maximum dose of $30 \times 10^6$ IU with no adverse effects.

Since the study was initiated, no patients have been withdrawn as a result of toxicity clearly resulting from the administration of Intron ® A or IFN-Con$_1$.

Determination of efficacy of IFN-con$_1$ and INTRON-A treatment

Antitumor response

Antitumor responses were assessed after four months of treatment using the AIDS Clinical Trials Group (ACTG) Oncology Committee's standard response criteria (Krown et al. J. Clin. Oncol. 7, 1201-1207 (1989)).

Immune functions

CD4 lymphocyte counts are taken every month for six months during the study to evaluate patients' immune response to HIV infection.

In all three treatment groups, the Kaposi's Sarcoma lesion responses and CD4 lymphocyte levels were equivalent.

EXAMPLE 3

Safety, Tolerance and Efficacy of IFN-con$_1$, Administered to Patients having Hepatitis C (HCV)

Improved Dose Tolerability

Treatment with type-one interferons causes several side effects which can limit the absolute doses patients can be given for treatment for a specific disease. These side effects include: flu-like symptoms, diarrhea, myelosuppression, elevated liver function tests, and mental status changes. These toxicities are rated according to the WHO (World Health Organization) scale as; grade I (mild), grade II (moderate), grade III (severe) and grade IV (life threatening). Toxicities from type one interferon treatment can range from grade I to grade IV. Any toxicity during type one interferon treatment judged to be non-tolerable by the patient or physician will result in a dose reduction or dose schedule modification. These dose modifications can lead to suboptimal treatment regimes which result in less than optimal efficacy. Consensus interferon allows for optimal dosing to be achieved and maintained over the course of treatment without accompanying dose limiting toxicity of any grade.

A clinical trial using consensus interferon to treat chronic Hepatitis C infection was initiated to study the effects of several doses of the drug. Patient data from consensus interferon treated patients were compared to data from patients with similar disease and demographic characteristics, treated with either Interferon-alpha 2a (Roferon ®) or Interferon-alpha 2b (Intron ®A) by the same principal investigator.

Study Design

The study included at least 30 patients infected with HCV exhibiting elevated (at least 1.5 times the upper limit of normal) alanine transferese (ALT: a liver enzyme) levels; the upper limit of normal in this study is 35 milliunits per milliliter (35 mu/mL). Additionally, efficacy of IFN-con$_1$ was evaluated by measuring antiviral activity via PCR analysis and by measuring ALT values during the course of treatment. Finally, historical data from HCV clinical studies of other recombinant interferons-alpha, specifically recombinant interferon-alpha-2a (Roferon ®) and alpha-2b (Intron ® A) was compared with data resulting from this study with respect to safety and changes in ALT values.

Eligible patients were enrolled into one of the IFN-con$_1$ dose cohorts summarized in Table 3.

TABLE 3

| IFN-con$_1$ Dose in Million Units (MU) | Doses/7-day Week* | No. Patients |
|---|---|---|
| 3 | 3 | 5 |
| 6 | 3 | 5 |
| 9 | 3 | 5 |
| 12 | 3 | 5 |
| 15 | 3 | 5 |

*Doses separated by at least 48 hours

Dose cohorts were enrolled sequentially with two-week intervals between the cohorts. Specifically, five patients were entered into the first cohort and were evaluated for a two week safety period if no Grade III or higher toxicity attributable to IFN-con$_1$ was observed, five patients were entered into the next cohort (6 MU). However, if any patient was observed to have Grade III or higher toxicity attributable to IFN-con$_1$, three additional patients were entered into the first cohort and were evaluated for two weeks. If no additional Grade III or higher toxicity attributable to IFN-con$_1$ was observed, patients were then entered into the next cohort (6 MU), but if any additional Grade III or higher toxicity attributable to IFN-con$_1$ was observed, patients were not entered into the next-higher dose cohort (6 MU). Escalation to the 9, 12, 15, 18, and 24 MU cohorts proceeded according to the same rules outlined above. In addition, if two or more patients experienced Grade III or higher toxicity attributable to IFN-con$_1$ at any dose level, no additional patients were enrolled in that cohort, and patients already on study treatment in that cohort or at a higher dose level were dose reduced to the dose level below that at which two or more Grade III or higher toxicities occurred. However, additional patients may continue to be enrolled (up to a total of 10 additional) at the dose level below that at which two or more Grade III or higher toxicities occurred.

If a patient in any of the cohorts experienced a Grade III toxicity attributable to IFN-con1 during or after the two-week initial evaluation, IFN--con1 was withheld until the toxicity diminished to Grade II or less. Treatment was then resumed at the next-lower dose-level. If the patient was receiving the 3 MU dose at the time of the Grade III toxicity, treatment was resumed at 2 MU. If any patient experienced a Grade IV toxicity attributable to IFN-con1, the patient was withdrawn from study. Patients were allowed to undergo three dose reductions during the course of study treatment (but not dosed-reduced below a dose level of 2 MU). Any patient requiring a fourth dose reduction for toxicity would be withdrawn from study treatment. Fever and chills lasting less than 24 hours, fatigue, headache, or Grade II or less toxicity were not considered dose-limiting toxicities unless they were determined to be intolerable to the individual patient. The drug was home-administered by either the patient or a third party (after successful completion of training).

Patients were evaluated at three months for response based on ALT level changes.

RESULTS

Patients were entered and enrolled into the cohorts described above. No dose limiting toxicities were observed in any patients during the first two weeks for the 3, 6, 9 and 12 MU dose groups respectively. One dose limiting toxicity was observed in one patient receiving 15 MU within the first two weeks of dosing. The observed toxicity was Grade II intolerable "flu-like" symptoms. The patient was dose reduced to 12 MU.

Dose limiting toxicities for the 12 week treatment period for each of the cohorts and the historical IFN-alpha 2 patients were as follows:

TABLE 4

| | Dose of IFN-con1 (Million Units) | Per Cent DLTs | Toxicity |
|---|---|---|---|
| n=4 | 3 | 0 | — |
| n=5 | 6 | 0 | — |
| n=5 | 9 | 0 | — |
| n=5 | 12 | 20% | "Flu-like" |
| n=5 | 15 | 20% | "Flu-like" |
| n=19 | 3 MU IFN-alpha 2 | 32% | "Flu-like" |

As illustrated by the above table, patients receiving IFN-con1at doses between 3 and 15 MU three times weekly experienced fewer dose limiting toxicities than patients receiving IFN-alpha 2. Since IFN--alpha 2 is only approved up to 3 MU for this indication, it was not possible to make a clinical comparison at higher dose levels of IFN-alpha 2. However, it is expected that the number of DLT's would be substantially higher for IFN-alpha 2 at higher dose levels.

TABLE 5

| | Response after 12 weeks of treatment | |
|---|---|---|
| | Dose of IFN-con1 (Million Units) | Response Rate * |
| n=4 | 3 | 25% |
| n=5 | 6 | 60% |
| n=5 | 9 | 80% |
| n=5 | 12 | 60% |
| n=4 | 15 | 75% |
| n=19 | 3 MU IFN-alpha 2 | 47% |

* Complete plus partial responses

As illustrated by the above table, patients receiving IFN-con1at doses between 3 and 15 MU three times weekly had ALT response rates that were at least as good as those observed with 3 MU of IFN-alpha 2.

The above demonstrates that treatment with IFN-con1results in a favorable efficacy rate with greater drug tolerability compared to treatment with IFN-alpha 2.

While the present invention has been described in terms of the preferred embodiments, it is understood that variations and modifications will occur to those skilled in the art. Therefore, it is intended that the appended claims cover all such equivalent variations which come within the scope of the invention as claimed.

What is claimed is:

1. A method for treating a patient having a viral disease selected from the group consisting of hepatitis A, hepatitis B, hepatitis C or hepatitis Delta while reducing the occurrence of Grade 3or 4 toxicities associated with alpha interferon treatment as measured by the World Health Organization toxicity scale, which comprises administering to said patient a therapeutically effective amount of a consensus human leukocyte interferon.

2. A method according to claim 1, wherein said viral disease is hepatitis A.

3. A method according to claim 1, wherein said viral disease is hepatitis B.

4. A method according to claim 1, wherein said viral disease is hepatitis C.

5. A method according to claim 1, wherein said viral disease is hepatitis Delta.

6. A method for treating a patient having Kaposi's Sarcoma while reducing the occurrence of Grade 3 or 4 toxicities associated with alpha interferon treatment as measured by the World Health Organization toxicity scale, which comprises administering to said patient a therapeutically effective amount of a consensus human leukocyte interferon.

7. A method according to claim 1 or 6, wherein said toxicities are selected from the group consisting of headache, fever, chills, nausea, anorexia. depression, and insomnia.

8. A method according to claim 1 or 6, wherein the consensus human leukocyte interferon is :;elected from the group consisting of IFN-con$_1$, IFN-con$_2$, and IFN-con$_3$.

9. A method according to claim 1 or 6, wherein the consensus human leukocyte interretort is ZFN-con$_1$.

10. A method according to claim 1 or 6, wherein the consensus human leukocyte interferon is a product of procaryotic expression of an exogenous DNA sequence.

11. A method according to claim 1 or 6, wherein the therapeutically effective amount is administered by a route of administration selected from the group consisting of oral, intravenous, intramuscular. subcutaneous, intranasal, and intralesional.

12. A method according; to claim 1 or 6, wherein the therapeutically effective amount of consensus human leukocyte interferon is from $2 \times 10^6$ to $30 \times 10^6$ units per patient.

13. A method according to claim 1 or 6, wherein the therapeutically effective amount of consensus human leukocyte interferon is from $6 \times 10^6$ to $15 \times 10^6$ units per patient.

14. A method according to claim 1 or 6, wherein the patient is a human.

15. A method according to claim 1 or 6, further comprising administering a therapeutically effective amount of a chemotherapeutic agent.

16. A method according to claim 1 or 6, further comprising administering: a therapeutically effective amount of G-CSF.

* * * * *